(12) United States Patent
Suzuki et al.

(10) Patent No.: US 7,671,600 B2
(45) Date of Patent: Mar. 2, 2010

(54) GAS CONCENTRATION DETECTION APPARATUS HAVING FUNCTION FOR DETECTING SENSOR ELEMENT ACTIVATION STATUS

(75) Inventors: Toshiyuki Suzuki, Handa (JP); Tomoo Kawase, Aichi-ken (JP); Eiichi Kurokawa, Okazaki (JP); Yohei Kawaki, Toyota (JP)

(73) Assignee: DENSO CORPORATION, Kariya (JP)

( * ) Notice: Subject to any disclaimer, the term of this patent is extended or adjusted under 35 U.S.C. 154(b) by 339 days.

(21) Appl. No.: 11/907,556

(22) Filed: Oct. 15, 2007

(65) Prior Publication Data

US 2008/0094079 A1  Apr. 24, 2008

(30) Foreign Application Priority Data

Oct. 20, 2006  (JP) .............................. 2006-285821

(51) Int. Cl.
 *G01N 27/62* (2006.01)
(52) U.S. Cl. ...................................... 324/466; 324/465
(58) Field of Classification Search ................. 324/464, 324/465; 204/407, 424; 205/781, 782, 783
See application file for complete search history.

(56) References Cited

U.S. PATENT DOCUMENTS

| 4,376,026 | A | * | 3/1983 | Hoffman et al. ............ 204/407 |
| 4,419,190 | A | | 12/1983 | Dietz et al. |
| 4,795,968 | A | * | 1/1989 | Madou et al. ................. 422/88 |
| 6,712,054 | B2 | | 3/2004 | Hosoya et al. |
| 7,017,567 | B2 | | 3/2006 | Hosoya et al. |

FOREIGN PATENT DOCUMENTS

| JP | S57-187646 | 11/1982 |
| JP | 2000-081414 | 3/2000 |
| JP | 2000-014079 | 1/2002 |
| JP | 2002-014079 | 1/2002 |

* cited by examiner

*Primary Examiner*—Vincent Q Nguyen
(74) *Attorney, Agent, or Firm*—Nixon & Vanderhye, PC

(57) ABSTRACT

A gas concentration detection apparatus includes a series-connected combination of a sensor element and a resistor, with an AC voltage being applied to one of the outer terminals of that combination and with the other outer terminal being held at a fixed potential. A DC voltage signal at a level determined by an oxygen concentration that is detected by the sensor element, and an AC voltage signal at an amplitude determined by sensor element impedance and hence by the sensor element activation status, are extracted from the series-connected combination by respectively separate circuits which apply separately determined amplification factors.

9 Claims, 8 Drawing Sheets

GAS CONCENTRATION DETECTION APPARATUS HAVING FUNCTION FOR DETECTING SENSOR ELEMENT ACTIVATION STATUS

CROSS-REFERENCE TO RELATED APPLICATIONS

This application is based on and incorporates herein by reference Japanese Patent Application No. 2006-285821 filed on Oct. 20, 2006.

BACKGROUND OF THE INVENTION

1. Field of Application

The present invention relates to a gas concentration detection apparatus, and in particular to a gas concentration detection apparatus for detecting concentrations of gaseous components such as oxygen, etc., in an exhaust gas of an internal combustion engine.

2. Description of the Prior Art

Types of gas concentration detection apparatus are known that are utilized as an air/fuel ratio sensor (generally abbreviated to A/F sensor) for the engine of a vehicle, with such a sensor detecting the concentration of oxygen in the exhaust gas from the engine. In particular, a planar type of A/F sensor is known, having a sensor element containing a layer of solid electrolyte, with a pair of electrodes mounted on that layer. When a voltage is applied between the electrodes, a current flows through them at a level determined by the concentration of oxygen in the exhaust gas. The air/fuel ratio of the exhaust gas is measured based on the level of that current.

With such an A/F sensor it is necessary for the sensor to be in an activated condition in order to accurately detect the oxygen concentration. The impedance of the sensor element (i.e., at any specific value of AC frequency) varies in accordance with the activation status of the sensor element, and hence the impedance can be measured to evaluate the activation status of the element. One method known in the prior art for measuring the oxygen concentration and the sensor element impedance concurrently, is to apply an AC voltage across the sensor element electrodes and to detect the amplitude of a resultant AC current that flows through the sensor. Such a method is described for example in Japanese patent application second publication No. 4-24657 (referred to in the following as reference document 1). An example of a circuit configuration for implementing such a detection method is shown in FIG. 10.

In FIG. 10, one terminal of a sensor element 60 is connected in series with a current measurement resistor 63, an oscillator 62 and a reference voltage source 61 (with the reference voltage source 61 being connected between the oscillator 62 and ground potential as shown), while the other terminal of the sensor element 60 is connected to ground potential. The input terminals of a differential amplifier 65 are connected across the terminals of the differential amplifier 65, and the output signal of the differential amplifier 65 is transferred through a LPF 66 and through a HPF 67. With the sensor element 60 exposed to an exhaust gas, when an AC voltage and superimposed DC voltage are applied to the sensor element 60 by the oscillator 62 and reference voltage source 61 and a resultant sensor current flows in the sensor element 60, the current contains a component (DC component) at a level determined by the oxygen concentration in the exhaust gas and a component (AC component) having an amplitude determined by the impedance of the sensor element 60. A differential voltage signal varying in proportion to the sensor current appears between the terminals of the current measurement resistor 63, with that differential voltage signal being supplied to the differential amplifier 65, to be amplified and converted to a voltage signal which varies with respect to the system ground potential.

A DC voltage signal component (corresponding to the DC component of the sensor current whose level is determined by the oxygen concentration) is extracted from the output of the differential amplifier 65 by the LPF 66, while an AC voltage signal component (corresponding to the AC component of the sensor current, whose amplitude is determined by the sensor impedance) is extracted by the sensor element 60 from the output of the differential amplifier 65. That AC voltage signal is rectified by a rectifier circuit 68, to obtain a voltage signal that varies in level in accordance with the impedance of the sensor element 60.

These output (analog) voltage signals from the LPF 66 and rectifier circuit 68 are inputted to a calculation apparatus (digital processing apparatus) such as a microcomputer, with the signals being converted to digital form in the calculation apparatus or before being inputted to the calculation apparatus. The calculation apparatus calculates the respective values of the air/fuel ratio and the sensor element impedance based on these input signals.

In general, there will be a large difference between the respective levels of the sensor current component that varies in accordance with the oxygen concentration and the sensor current component that varies in accordance with the sensor element impedance. As a result, the voltage signal component (inputted from the current measurement resistor 63 to the differential amplifier 65) representing the air/fuel ratio will be substantially smaller (in some cases, by an order of magnitude) than the voltage signal component that varies in accordance with the sensor element impedance.

Hence if for example the degree of amplification is determined based on the expected range of variation of the voltage signal component corresponding to the air/fuel ratio, the variations in amplitude of the voltage signal component corresponding to the sensor element impedance may exceed the range of values that can be amplified by the differential amplifier 65. This will not only result in a lowered accuracy of detecting the sensor element impedance, but will also result in a lowering of the accuracy of detecting the air/fuel ratio. That is to say, although the air/fuel ratio detection signal is extracted by averaging the output signal from the differential amplifier 65 using a LPF 66, if the upper limit of the range of amplification of the differential amplifier 65 is exceeded, the resultant signal from the LPF 66 will not accurately represent the average value, causing errors in the measured air/fuel ratio.

Conversely if the degree of amplification were to be predetermined based on the expected range of variation of the amplitude of the AC voltage signal component that varies in accordance with the sensor element impedance, then it would not be possible for the differential amplifier 65 alone to apply sufficient amplification to the air/fuel ratio detection component. Hence it would be necessary to utilize an additional amplifier stage to further amplify the voltage signal component used for air/fuel ratio detection. However this will result in the problem of an increase in amplifier offset voltage, which could cause a lowering of accuracy of air/fuel ratio detection.

SUMMARY OF THE INVENTION

It is an objective of the present invention to overcome the above problems of the prior art, by providing a gas concentration detection apparatus whereby detection of a concentration of a constituent gas in an exhaust gas and also detection of the impedance of a sensor element of the apparatus can both be performed to a high degree of accuracy.

To achieve the above objective, the invention provides a gas concentration detection apparatus having a sensor element which incorporates a solid electrolyte layer and is responsive to an applied voltage for passing a sensor current that varies in level in accordance with the concentration of a specific constituent gas (such as oxygen) in a test-object gas (such as the exhaust gas of an internal combustion engine). A current measurement resistor is connected in series with the sensor element, i.e., with respective terminals of the current measurement resistor and the sensor element being connected at a connection point. An AC voltage source applies an AC voltage to one of the outer terminals of the series-connected combination of the resistance and sensor element, while a reference voltage source applies a fixed DC voltage to the other outer terminal of that series-connected combination.

As a result, a current which flows through that series-connected combination is made up of a DC current component and an AC current component. The term "DC current component" as used herein signifies a current component having a maximum frequency of variation that is substantially lower than that of the applied AC voltage. The DC current component varies in accordance with the concentration of the specific constituent gas and the AC current component varies in accordance with the impedance (i.e., impedance at the frequency of the AC voltage) of the sensor element.

Specifically, as described above the sensor element impedance varies in accordance with whether the sensor element is in activated, so that the amplitude of the AC current component is indicative of that activation status.

A first detection signal output circuit is coupled to the current measurement resistor, for deriving a DC voltage signal component corresponding to the aforementioned DC current component, to thereby obtain a first measurement signal, with that first measurement signal varying in level accordance with the constituent gas concentration. A second detection signal output circuit is coupled to the aforementioned connection point between the current measurement resistor and the sensor element, for deriving an AC voltage signal component corresponding to the aforementioned AC current component, and thereby obtaining the second measurement signal, with the level of the second measurement signal varying in accordance with the sensor element impedance.

In that way, with the first and second detection signal output circuits incorporating respective amplifier circuits, and configured as respectively separate systems, the DC voltage signal component indicative of the constituent gas concentration and the AC voltage signal component indicative of the sensor element impedance can be amplified by respectively different appropriate degrees of amplification. This is advantageous in achieving a higher degree of accuracy in detecting both the voltage signal component indicative of the constituent gas concentration and the voltage signal component indicative of the sensor element impedance, due to the large difference in magnitudes between these voltage signal components.

More specifically, with the applied AC voltage and the applied DC voltage of the aforementioned series-connected combination being each applied with respect to the reference ground potential of the apparatus, the voltage at the aforementioned connection point varies with respect to that ground potential in accordance with the current that flows through the series-connected current measurement resistor and sensor element.

With the present invention, it is possible to extract the DC voltage signal component as a differential voltage appearing across the current measurement resistor, i.e., by connecting respective inputs of a differential amplifier (via LPFs) to the terminals of that resistor. However preferably, an input terminal of the first detection signal output circuit is coupled to the connection point between the current measurement resistor and the sensor element, for deriving the voltage signal component corresponding to the DC current component as a signal that varies with respect to ground potential.

BRIEF DESCRIPTION OF THE DRAWINGS

FIGS. 8(a), 8(b), 8(c) are partial circuit diagrams for describing respective alternative configurations of the first embodiment;

DESCRIPTION OF PREFERRED EMBODIMENTS

An embodiment of a gas concentration detection apparatus will be described in the following, which is applicable to detecting the concentration of oxygen in the exhaust gas from an internal combustion engine, for thereby detecting the air/fuel ratio at which the engine is operating. The results obtained from detecting the air/fuel ratio can for example be utilized by an air/fuel ratio control system of a vehicle engine ECU (electronic control unit), etc. Such a system may apply control to maintain a stoichiometric value of air/fuel ratio, or to maintain the air/fuel ratio within a specific range of lean values, by feedback control. The term "lean" air/fuel ratio signifies that the engine is operating with an air/fuel ratio having a higher concentration of oxygen than the stoichiometric air/fuel ratio, and hence a higher concentration of oxygen in resultant exhaust gas than for the stoichiometric value. Conversely a "rich" air/fuel ratio signifies an air/fuel ratio having a lower concentration of oxygen than for the stoichiometric value.

Figure 2:
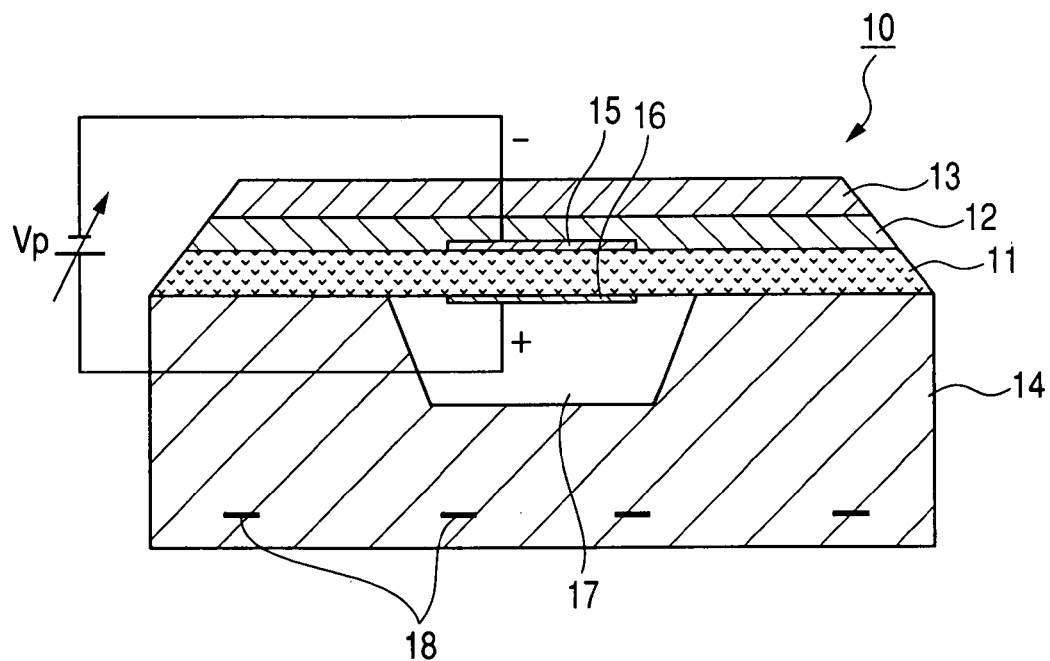
FIG. 2 is a cross-sectional view of a sensor element used in the embodiment of FIG. 1.

The configuration of the air/fuel ratio sensor element will be described referring first to the cross-sectional view of FIG. 2, showing the multi-layer structure of a sensor element 10.

The sensor element 10 is of multi-layer planar configuration, extending in a direction at right angles to the plane of the paper as seen in FIG. 2, and is contained within a housing (not shown in the drawings).

The sensor element 10 is formed of a solid electrolyte layer 11, a diffusion resistance layer 12 and a gas shield layer 13, successively formed from bottom to top, upon a insulation layer 14. The outer surface of the sensor element is covered by a protective layer (not shown in the drawings). The solid electrolyte layer 11 is a rectangular sheet of partially stabilized zirconia which has electrodes 15 and 16 respectively formed on its upper and lower faces. The diffusion resistance layer 12 is a sheet of porous material for passing the exhaust gas to the electrode 15 by diffusion, and the gas shield layer 13 is a thin layer of porous material which controls the diffusion of the exhaust gas. Each of the layers 12 and 13 is formed as a sheet of a ceramic such as alumina, spinel, zirconia, etc., formed with micropores (i.e., small capillaries). The layers 12 and 13 have respectively different degrees of porosity, by having different values of diameter and/or density of the micropores, to provide respectively different rates of gas diffusion.

The insulation layer 14 is formed of a ceramic material such as alumina, having a high thermal transfer coefficient, and is formed with an atmosphere duct 17 (leading to the outer air) formed in the face that opposes the solid electrolyte layer 11, located to expose the electrode 16. A heater element 18 is embedded in the insulation layer 14, formed of wire that is heated by a current supplied from a battery (not shown in the drawings) to effect overall heating of the sensor element.

In use, the sensor element 10 is surrounded by exhaust gas which, reaches the electrode 15 by diffusion through the gas shield layer 13 and the diffusion resistance layer 12. When the exhaust gas is lean (i.e., due to the air/fuel ratio being lean), oxygen in the exhaust gas is ionized by the electrode 15, and a resultant oxygen ion current flows from the electrode 15 to the electrode 16, with the oxygen then being discharged into the atmosphere duct 17 by the electrode 16. If the exhaust gas is rich (i.e., due to the air/fuel ratio being rich) the oxygen in the gas within the atmosphere duct 17 is ionized by the electrode 16, and an oxygen ion current flows from the electrode 16 to the electrode 15, with oxygen thereby being discharged by the electrode 15 to the exhaust gas side of the sensor element.

Figure 3:
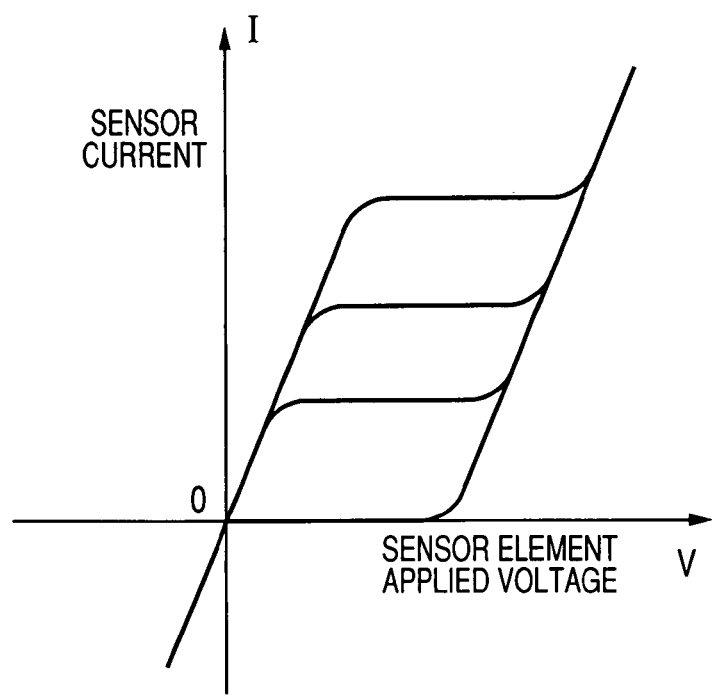
FIG. 3 illustrates voltage/current characteristics of an air/fuel ratio sensor.

FIG. 3 is a diagram showing the voltage/current characteristics of such an A/F sensor, where the voltage is a fixed DC value (with the present invention, an average fixed DC value, as described hereinafter) applied between the terminals of the sensor. In FIG. 3, straight-line portions which are parallel to the voltage axis (horizontal axis) correspond to a boundary current region of operation, in which the sensor current is determined only by the air/fuel ratio. Changes in the level of sensor current correspond to increases or decreases in the air/fuel ratio, i.e., the more lean the air/fuel ratio becomes, the higher will be the sensor current, while the more rich the air/fuel ratio becomes, the lower will be the sensor current. By applying a DC voltage across the sensor element 10 which results in values of sensor current that are within the boundary current region, the level of sensor current can be appropriately measured.

It can thus be understood that with an appropriate DC voltage applied between the electrodes of such a sensor element, the sensor element passes a level of current in accordance with the oxygen concentration in the test-object gas (exhaust gas), i.e., passes a concentration-indicative current.

The main portions of the sensor circuit of the embodiment will be described referring to FIG. 1. As shown, a reference voltage source 21 produces a fixed DC voltage of +2.6 V with respect to ground potential, which is applied via an operational amplifier 22 to the positive terminal (S+ terminal) of the sensor element 10. The negative (S−) terminal of the sensor element 10 is connected to one terminal of a resistor 26. A reference voltage source 23 and an oscillator 24 are connected in series between ground potential and the second terminal of the current measurement resistor 26. The oscillator 24 generates an AC voltage at a frequency in the range 10~20 kHz and 2 V amplitude, while the reference voltage source 23 produces a fixed DC voltage of +2.2 V with respect to ground potential. Hence, an AC voltage is applied to the second terminal of the current measurement resistor 26, which varies by ±1 V with respect to a DC level of +2.2 V (i.e., the average level of the AC voltage is +2.2 V). Thus there is a difference of +0.4 V between the DC voltage applied to the S+ terminal of the sensor element 10 and the average level of the AC voltage applied to the current measurement resistor 26 from the operational amplifier 25. An appropriate value of (average) DC voltage is thereby applied across the sensor element 10, for performing sensor current measurement within the boundary region described above referring to FIG. 3.

Capacitors 28 and 20 are connected between ground potential and the positive terminal S+ and the negative terminal S− of the sensor element 10, respectively, to suppress electrical noise.

Two measurement signal output sections 31 and 32 are connected to the junction of the current measurement resistor 26 and the negative terminal S− of the sensor element 10. The amplitude of an AC voltage component (i.e., an impedance-indicative voltage) appearing at that junction is determined by the ratio of the resistance of the current measurement resistor 26 to the impedance of the sensor element 10 (where "impedance" here signifies the impedance presented at the frequency of the AC voltage). The A/F ratio detection section 31 derives an output signal indicative of the oxygen concentration in an exhaust gas that is being subjected to detection (with such a gas being referred to in the following and in the appended claims as the detection-object gas). The output signal thereby obtained by the A/F ratio detection section 31 will be referred to as the air/fuel ratio detection signal. The sensor element impedance detection section 32 derives an output signal indicative of the aforementioned impedance of the sensor element 10, referred to in the following as the impedance detection signal.

As shown, the A/F ratio detection section 31 is made up of a LPF (low-pass filter) 7 formed of an operational amplifier 33, resistors 1 and 2, and a capacitor 6, with the resistor 1 and capacitor 6 connected between the inverting input terminal and output terminal as a filter circuit 34. The LPF 7 functions as an amplifier circuit at frequencies below the LPF cut-off frequency, with the amplification factor at DC being determined by the values of resistors 1 and 2 (specifically, the ratio of these resistor values).

The sensor element impedance detection section 32 is made up of a HPF (high-pass filter) 35, an amplifier circuit 8 formed of an operational amplifier 5 and resistors 3, 4, and a P/H (peak-hold) circuit 36. The P/H circuit 36 detects peak values of an amplified AC voltage signal extracted by the HPF 35, to produce the impedance detection signal.

The air/fuel ratio detection signal that is outputted from the A/F ratio detection section 31 is supplied to a microcomputer 38, together with the impedance detection signal from the sensor element impedance detection section 32. The microcomputer 38 is a usual type of digital processor apparatus (microcomputer), having a CPU, memory devices, etc., but also incorporates an A/D converter for converting each of the air/fuel ratio detection signal and the impedance detection signal (i.e., respective analog signals) to digital signals. Alternatively, an A/D converter that is external to the microcomputer 38 could be utilized.

Signal voltage amplification is performed in both the A/F ratio detection section 31 and the sensor element impedance detection section 32, applying respectively different amplification factors. The amplification factors are established in accordance with the range of input signal voltages (with this embodiment, 0~5 V) that can be handled by the A/D converter in the microcomputer 38. With this embodiment the amplification factor of the A/F ratio detection section 31 is set within the range from 10 to 20, while that of the sensor element impedance detection section 32 is set as 5.

A reference voltage source 37 applies a fixed positive voltage to the non-inverting input terminal of the operational amplifier 33 for setting the output signal voltage level from the A/F ratio detection section 31 appropriately, e.g., to be at the center of the aforementioned 0~5 V input signal range when the DC level of the voltage at the junction between the resistor 26 and sensor element 10 corresponds to a stoichiometric air/fuel ratio.

As a result of the AC voltage applied by the oscillator 24 to the sensor element 10, a sensor current flows in the sensor element 10, with the sensor current being a combination of a first (DC) current component, i.e., the aforementioned concentration-indicative current, whose level is determined by the oxygen concentration in the exhaust gas, and a second (AC) current component whose level is determined by the impedance of the sensor element 10. The junction point (i.e., connection point) between the sensor element 10 and the current measurement resistor 26 is used as a measurement point for detecting these respective sensor current components as respective voltage signal components, to thereby derive the air/fuel ratio detection signal and the impedance detection signal. Specifically, the voltage at that junction point is an AC voltage (at the frequency of the AC voltage generated by the oscillator 24) superimposed on a DC voltage (more specifically, a voltage whose maximum frequency of variation is substantially lower than the AC voltage frequency), with the junction point voltage varying in proportion to the sensor current. The A/F ratio detection section 31 extracts the DC voltage component (varying with respect to the circuit ground potential) at the junction point, and amplifies it to obtain the air/fuel ratio detection signal that is supplied to the microcomputer 38. The sensor element impedance detection section 32 extracts the AC component of the voltage at the junction point between the sensor element 10 and current measurement resistor 26 (as a voltage varying with respect to ground potential), and detects the peak values of the extracted AC component after amplification, to obtain the impedance detection signal that is supplied to the microcomputer 38.

The microcomputer 38 processes the air/fuel ratio detection signal to calculate the air/fuel ratio of the exhaust gas, and processes the impedance detection signal to calculate the impedance of the sensor element 10 at that point in time.

It can thus be understood that the A/F ratio detection section 31 and sensor element impedance detection section 32 constitute two separate systems for extracting respective signal components from a voltage signal that appears at the junction between the sensor element 10 and the current measurement resistor 26, with that voltage signal varying in accordance with the current which flows in the sensor element 10, and with the extracted voltage signal components being processed to respectively detect the air/fuel ratio of the exhaust gas and the impedance of the sensor element 10. As a result of utilizing two separate systems in that manner, respective appropriate degrees of amplification can be applied in these systems.

Figure 10:
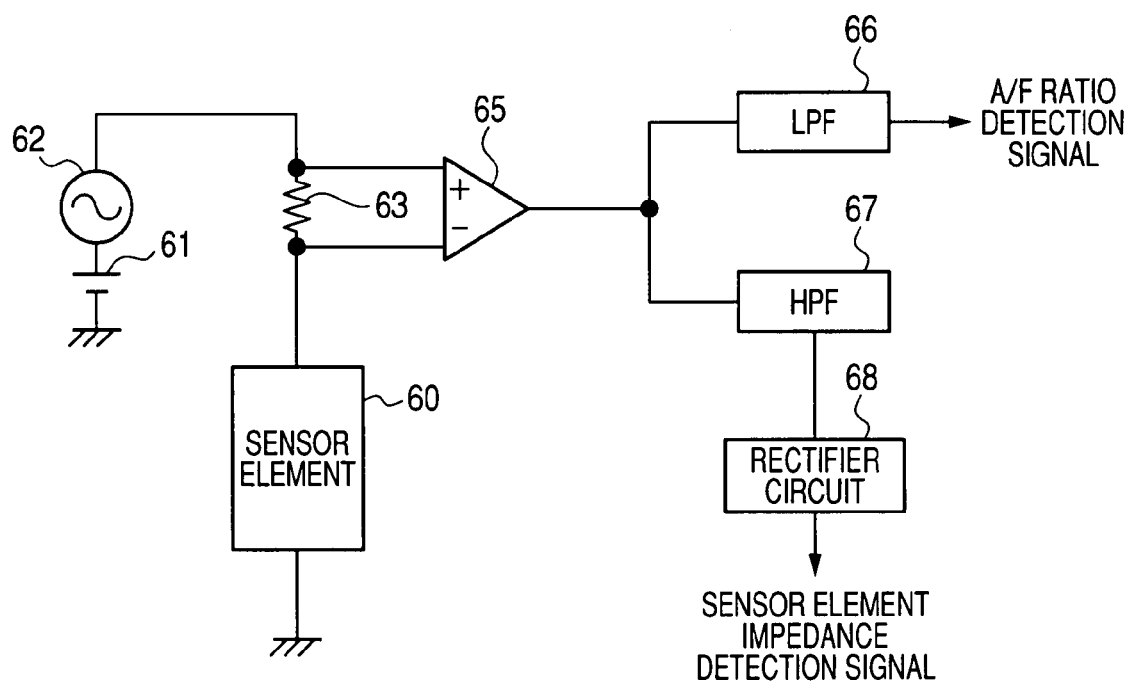

On the other hand in the case of prior art technology such as that shown in FIG. 10, if the expected variation range of the air/fuel ratio detection signal component is used as a basis for determining the signal amplification factor, the accuracy of detecting the sensor element impedance is reduced, whereas if the expected variation range of the impedance detection signal component is used as a basis for determining the amplification factor, then the accuracy of detecting the air/fuel ratio becomes reduced.

Figure 4A:
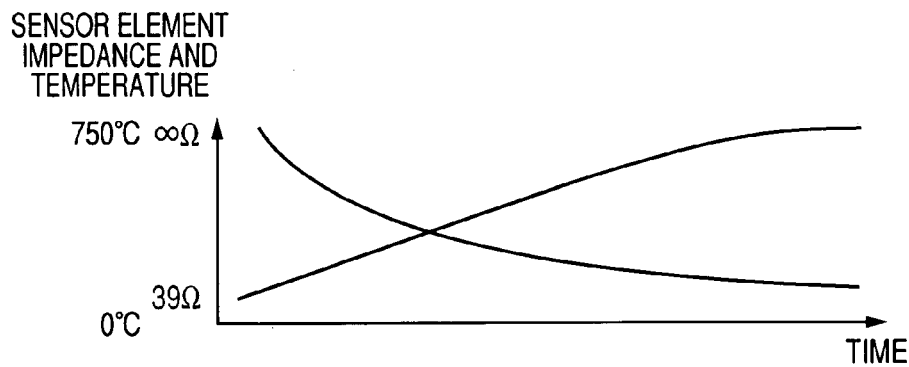
FIGS. 4(a), 4(b), 4(c), 4(d), 4(e) are timing diagrams for describing the operation of the first embodiment, showing changes that occur in circuit parameters as the temperature of the sensor element increases.
Figure 4B:
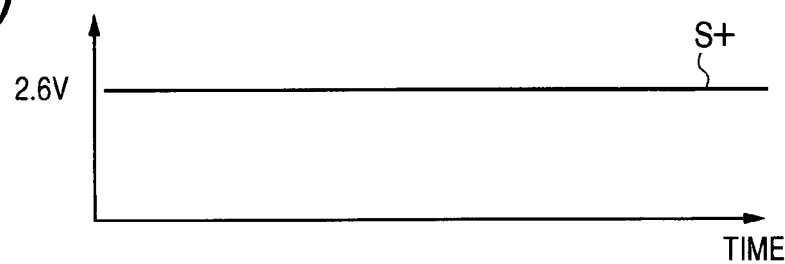
Figure 4C:
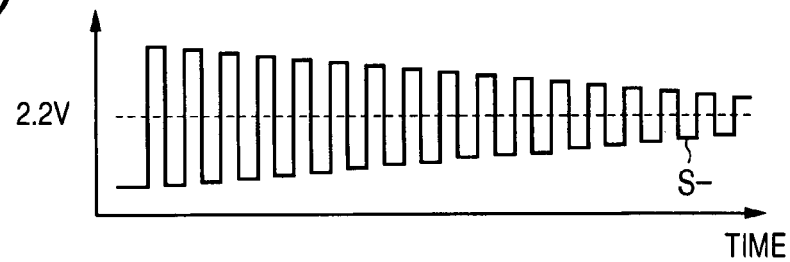
Figure 4D:
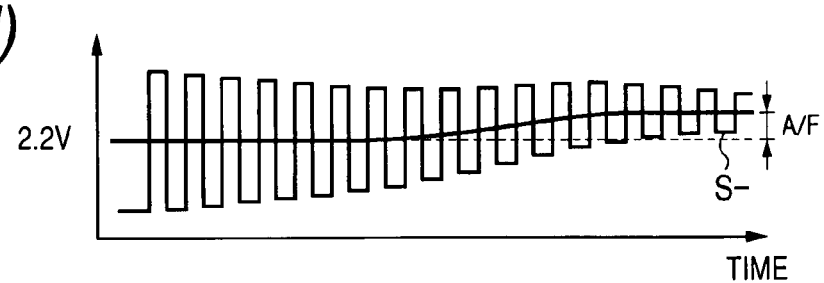
Figure 4E:
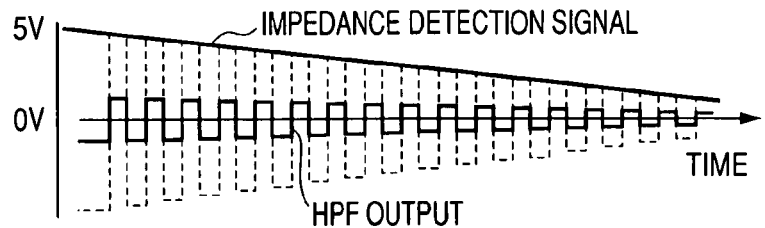

FIGS. 4(a) to 4(e) are timing diagrams illustrating changes which occur in respective parameters as the temperature of the sensor element 10 increases, immediately after the vehicle engine is started from a cold condition. FIG. 4(a) illustrates the corresponding changes which occur in the sensor element impedance and sensor element temperature, while FIG. 4(b) illustrates corresponding changes that occur in the voltage at the S+ terminal of the sensor element 10. Each of FIGS. 4(c), 4(d) show corresponding changes that occur in the voltage at the S− terminal of the sensor element 10 (i.e., junction point between the sensor element 10 and the current measurement resistor 26) for respectively different values of air/fuel ratio. FIG. 4(e) illustrates the corresponding changes that occur in the output signal from the sensor element impedance detection section 32 (impedance detection signal).

FIG. 4(c) illustrates the case in which the air/fuel ratio is the stoichiometric value, while FIG. 4(d) illustrates a case in which the air/fuel ratio is lean.

When engine starting is performed and supplying of heating current to the sensor element 10 is started, the temperature of the sensor element 10 is initially close to the ambient temperature, so that the element impedance is substantially high. Immediately after engine starting, the element temperature begins to gradually increase, due to heating from the exhaust gas from the engine and the heating resulting from current flow in the heater of the sensor element 10. The element impedance thereby gradually falls. On completion of activating the sensor element 10, the element temperature is approximately 750° C., and the element impedance is for example approximately 39 ohms.

With this embodiment, while the temperature of the sensor element 10 is increasing, the voltage at the S+ terminal of the sensor element 10 is fixed at 2.6 V and the voltage at the S+ terminal is varied at the frequency of the AC output from the oscillator 24. When the sensor element 10 is in an initial low-temperature condition, due to the very high impedance of the element, the amplitude of the AC component of the voltage at the S− terminal is substantially identical to the output AC voltage from the oscillator 24. Specifically, the voltage at the S− terminal varies in the positive direction and a negative direction with a peak amplitude of approximately 1 V, with respect to a central DC level (i.e., average voltage level) of approximately 2.2 V. As the temperature of the sensor element 10 increases and the element impedance decreases accordingly, the amplitude of the AC component of the voltage appearing at the S− terminal gradually falls.

In the case of a stoichiometric air/fuel ratio, the DC level (average level) of the S− terminal voltage remains constant at the average level of the applied AC voltage (2.2 V), as illustrated in FIG. 4(c). If the air/fuel ratio is lean, then as the sensor element 10 becomes activated, the sensor current increases so that the DC level of the voltage appearing at the S− terminal becomes increased (i.e., becomes more positive) as illustrated in FIG. 4(d). That is to say, a DC voltage component becomes superimposed on the voltage at the S− terminal of the sensor element 10 due to a DC current (sensor current) that flows through the sensor element. That DC voltage component is extracted by the A/F ratio detection section 31, to obtain the air/fuel ratio detection signal that is supplied to the microcomputer 38. As described above, "DC component" actually signifies a component which varies within a frequency range that is substantially lower than the frequency of the AC voltage.

Figure 5:
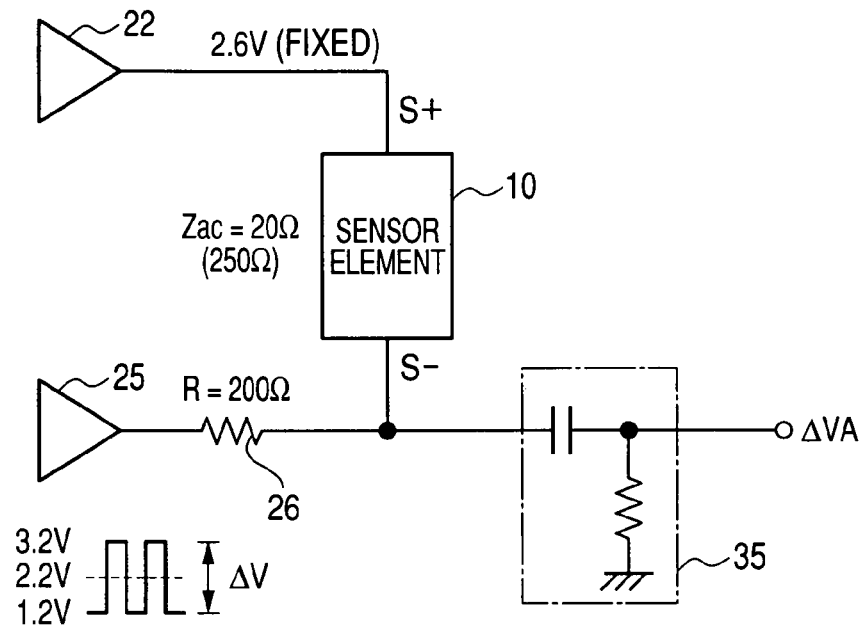
FIG. 5 is a partial circuit diagram corresponding to FIG. 1, showing examples of specific voltage and resistance values.

The AC component of the voltage appearing at the S− terminal is extracted by the HPF 35 of the sensor element impedance detection section 32 as illustrated in FIG. 4(*e*). As described above, the output signal from the HPF 35 is amplified only to an extent that the peak-to-peak amplitude of the amplified signal will not exceed the allowable input voltage range (5 V) of the A/D converter of the microcomputer 38. Peak detection of that amplified signal is performed by the peak-hold circuit 36, to obtain the impedance detection signal as shown in FIG. 5(*e*). The obtained impedance detection signal will be identical irrespective of whether the voltage appearing at the S− terminal is as shown in FIG. 4(*c*) or as in FIG. 4(*d*). In that way, air/fuel ratio detection and element impedance detection are performed concurrently by the apparatus.

Designating the element impedance as Zac, a specific method of calculating the sensor element impedance will be described referring to a numeric example shown in FIG. 5. Here it is assumed that the center level of the S− terminal voltage is 2.2V, the AC voltage amplitude is ±1 V with respect to that center value (i.e., the peak-to-peak amplitude $\Delta V$ is 2 V), the resistance R of the current measurement resistor 26 is 200Ω, and the impedance Zac of the sensor element 10 when activated is 20Ω. That is to say, it is assumed that when the sensor element 10 has become heated by the exhaust gas to attain its lowest value of impedance Zac, that value is 20Ω.

The output voltage from the HPF 35, which is the variation amplitude $\Delta VA$ of the AC component of the voltage appearing at the junction point between the current measurement resistor 26 and the sensor element 10, is expressed as:

$$\Delta VA = \Delta V \times Zac/(Zac+R) \quad (1)$$

With the above specific numeric values, $$\Delta VA = 2 \times 20/(20+200) = 0.182 \, [V]$$

If it is assumed that the value of Zac prior to activation of the sensor element 10 is 250Ω, then in that condition:

$$\Delta VA = 2 \times 250/(250+200) = 1.111 \, [V]$$

The microcomputer 38 calculates the impedance value Zac, after calculating $\Delta VA$ using equation (1) above, as follows:

$$Zac = \Delta VA \times R/(\Delta V - \Delta VA) \quad (2)$$

An amount of voltage change equal to the peak amplitude of the AC voltage (i.e., 1 V), at the junction between the current measurement resistor 26 and sensor element 10, corresponds to an amount of change $\Delta I$ in the current flow through that junction, where (after activation of the sensor element 10):

$$\Delta I = 1/(20+200) = 4.55 \, [mA]$$

That is to say, the peak value of current that must be supplied from the operational amplifier 25 is equal to the DC current component that flows through the sensor element 10 (whose level is determined by the air/fuel ratio) incremented by 4.55 ma.

For example designating the aforementioned DC current component as IL, if it is assumed that the maximum value which IL will attain is 2 mA then the peak value of current that must be supplied from the operational amplifier 25 is 6.55 mA.

Figure 6:
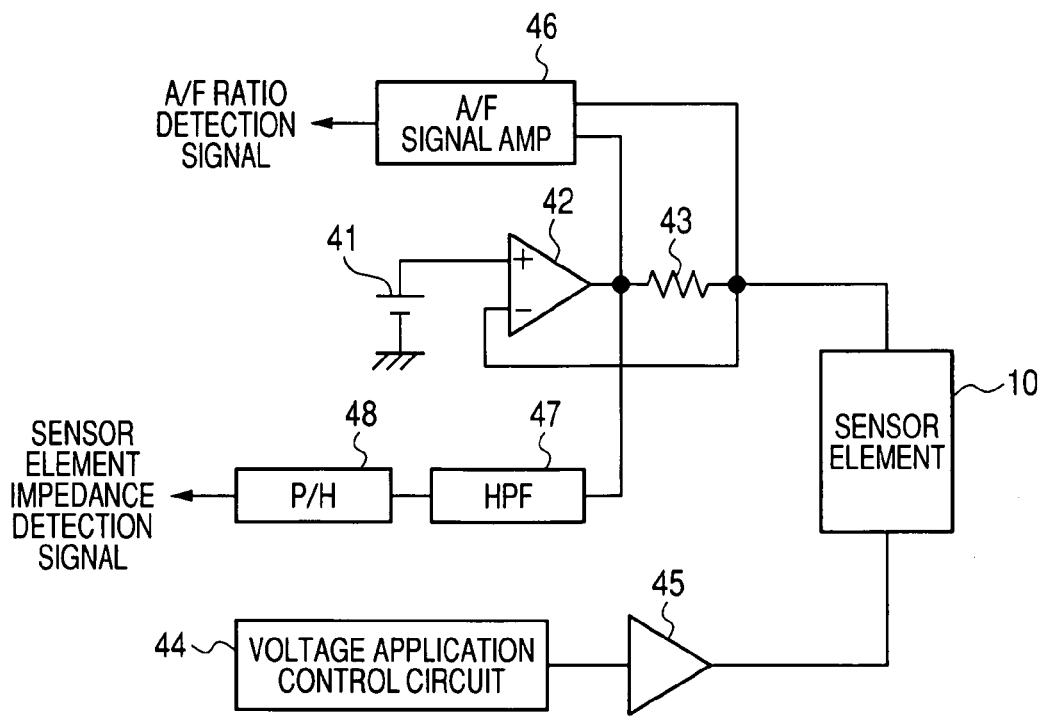
FIG. 6 is a circuit diagram for describing the operation of a prior art example of a gas concentration detection apparatus for air/fuel ratio detection.

Another example of a prior art type of air/fuel ratio sensor apparatus is shown in FIG. 6, which will be described for the purpose of comparison with the present invention. In FIG. 6, a reference voltage source 41, an operational amplifier 42 and a current measurement resistor 43 are connected to one terminal of a sensor element 10 as shown, while a voltage application control circuit 44 and an operational amplifier 45 are connected to the other terminal of the sensor element 10. When a sensor current flows in accordance with the air/fuel ratio of an exhaust gas, the sensor element current is measured based on a voltage that appears between the terminals of the current measurement resistor 43, with that voltage signal being amplified by the A/F ratio detection signal amplifier 46 and the resultant air/fuel ratio detection signal being supplied to a microcomputer (not shown in the drawings).

When impedance detection is performed, an excess voltage (an AC voltage at a predetermined frequency) is momentarily applied from the voltage application control circuit 44 and an impedance detection signal is obtained based on a change in current that occurs in response to that excess voltage. That is to say, as a result of the excess voltage being momentarily outputted, a corresponding change in current occurs, in accordance with the impedance of the sensor element 10 at that time. The amount of that change in current is measured by using the current measurement resistor 43. Signal processing is then performed by the HPF 47 and the peak-hold circuit 48 to extract a signal representing the amount of current change, and that signal is outputted to the microcomputer, as an impedance detection signal. The microcomputer then calculates the sensor element impedance based on the amount of voltage change and the amount of current change (as represented by the impedance detection signal).

With the configuration of FIG. 6, the impedance Zac of the sensor element is calculated based on the amount of voltage change $\Delta V$ and amount of current change $\Delta I$ occurring when the AC voltage is applied, i.e., $Zac = \Delta V/\Delta I$. In that case, the amount of voltage change $\Delta V$ is a fixed value, and if the sensor element impedance is low (i.e., due to the sensor element being in the activated condition) then the level of sensor current will be high. For example, if $\Delta V = 0.2$ V and $Zac = 20\Omega$ then the amount of current change $\Delta I$ will be 10 mA.

Hence with the circuit configuration of FIG. 6, again assuming that a maximum DC current of 2 mA will flow through the sensor, the peak level of current that must be supplied from the operational amplifier 45, to perform impedance detection, will be 12 mA (i.e., peak current=2 mA+10 mA) as compared with 6.5 mA for the above embodiment of the present invention. Thus with the above embodiment, substantially lower levels of current flow in the circuit, so that lower level of output current is required from the operational amplifier 25 than for the prior art example.

Hence the chip area of the operational amplifier 25 can be made small by comparison with that required for the operational amplifier 45 of the example of FIG. 6, i.e., the space occupied by transistors on the chip can be small, so that the overall size of the entire circuit of the embodiment (when implemented as in integrated circuit) can be made small. This is significant, in view of increasing demand for the ECU (engine control unit) of a motor vehicle to be made smaller in size.

Next, preferred ranges of value R for the resistance of the current measurement resistor 26 and for the amplitude $\Delta V$ of the AC voltage will be described referring to FIG. 7. FIG. 7(*a*)

illustrates the relationship between the resistance R of the current measurement resistor 26 and the air/fuel ratio detection error. FIG. 7(b) illustrates the relationship between the resistance R and the resolution of detecting the sensor element impedance. FIG. 7(c) illustrates the relationship between the sensor element current and the AC voltage amplitude ΔV. FIG. 7(d) illustrates the relationship between the AC voltage amplitude ΔV and the accuracy of detecting the sensor element impedance. FIGS. 7(c), 7(d) show measurement results obtained when the value of R is 200Ω.

Figure 7A:
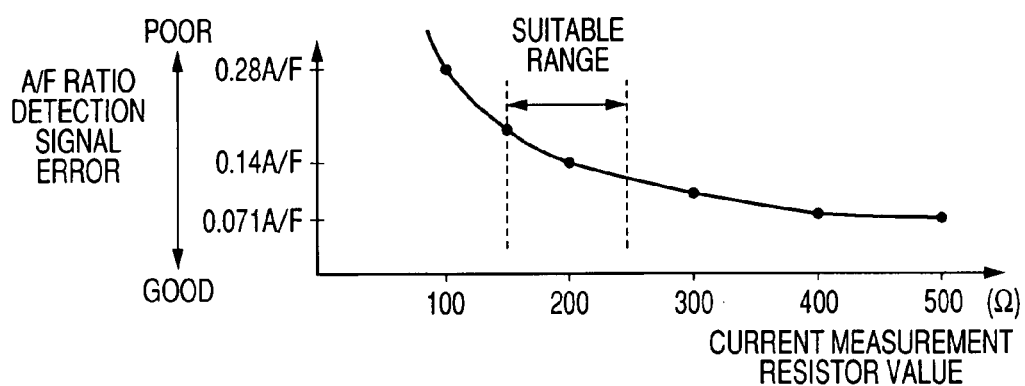
FIGS. 7(a), 7(b), 7(c), 7(d) are diagrams for describing specific preferred ranges of values for the resistance of a current measurement resistor and for the amplitude of an AC voltage, with the first embodiment.
Figure 7B:
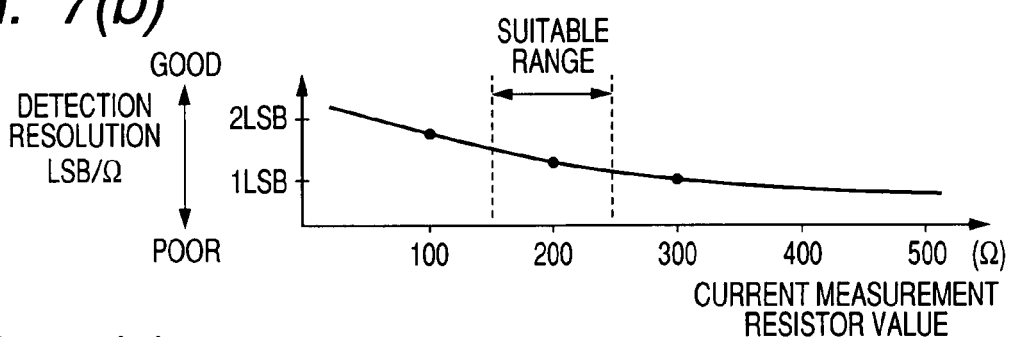
Figure 7C:
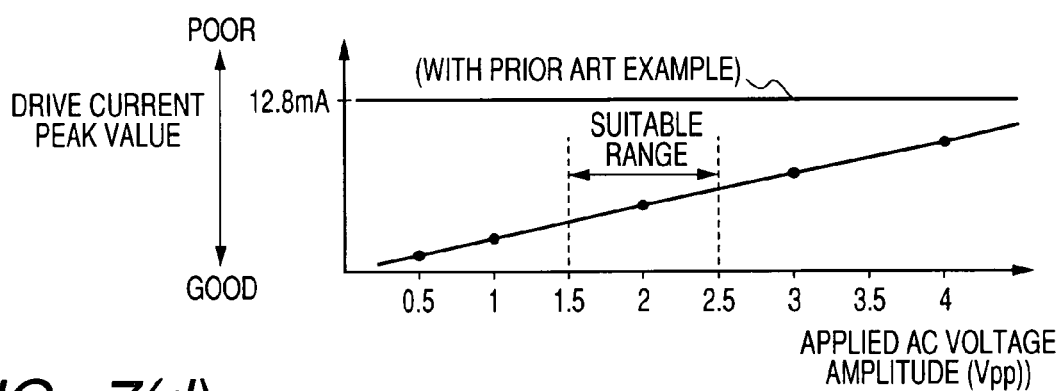
Figure 7D:
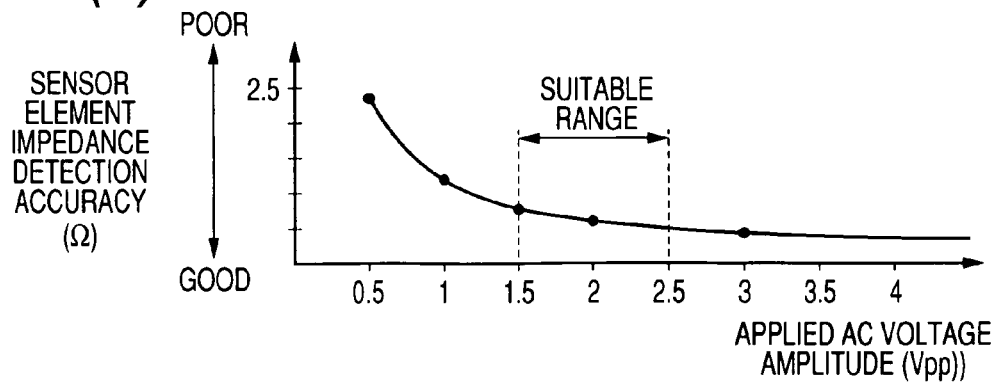

As shown in FIG. 7(a), the greater the value of the resistance R of the current measurement resistor 26, the more accurately can the air/fuel ratio be detected. On the other hand, as shown in FIG. 7(b), the greater the value of the resistance R, the lower will become the accuracy of detecting the sensor element impedance. Hence, based on these considerations, the optimum range of values for resistance R is 150~250Ω, and the optimum value is 200Ω.

Alternatively, the resistance of the current measurement resistor can be established based on the impedance of the sensor element when activated, i.e., the resistance of the current measurement resistor can be set as 5~10 times the value of the (activated) sensor element impedance Furthermore as shown in FIG. 7(c), the smaller the amplitude ΔV of the AC voltage, the smaller becomes the sensor element current, so that the amount of drive current required from the operational amplifier 25 is reduced accordingly, and hence the size of an integrated circuit containing the sensor circuit can be made smaller.

On the other hand, as the amplitude ΔV is made smaller, the lower becomes the accuracy of detecting the sensor element impedance. Hence, based on these considerations, the optimum range of values for the amplitude ΔV is 1.5~2.5 V, with the optimum value of ΔV being 2 V.

The frequency of the AC voltage will now be considered. Firstly, in the case of a sensor element having a solid electrolyte layer such as the sensor element 10, the AC frequency should be higher than 1 kHz, from considerations of the sensor characteristics. Furthermore it is necessary to use a HPF in the A/F ratio detection section 31 to extract the AC component of the measurement voltage signal (i.e., the voltage appearing at the junction between the sensor element 10 and the current measurement resistor 26), for deriving the impedance detection signal as described above. However variations in the amplitude of the measurement voltage signal, due to variations in the air/fuel ratio, occur at frequencies of approximately 100 kHz, depending upon the engine speed). Thus, in order to enable reliable discrimination between the AC component of the measurement voltage and the variations occurring in the measurement voltage due to changes in the air/fuel ratio, there must be a sufficient difference between the cut-off frequency of the LPF used to extract the air/fuel ratio variation components (i.e., the LPF 7 in FIG. 1) and the cut-off frequency of the HPF used to extract the AC component (i.e., the HPF 35 in FIG. 1).

From these considerations, the AC frequency generated by the oscillator 24 is preferably made at least 10 kHz.

In addition, the effects of the inductances of the wiring that interconnects the computers of the sensor circuit must also be taken into consideration, so that the AC frequency cannot be made excessively high. In addition, due to that fact and also based on the operating characteristics of an operational amplifier utilized as the operational amplifier 25, and taking into account manufacturing variations in component characteristics, 20 kHz can be considered as the upper limit for the AC frequency. Thus based on all of the above considerations, the AC frequency is preferably set within the range 10-20 kHz.

The following effects are obtained with the above embodiment. Due to the fact that the voltage signal appearing at the junction between the sensor element 10 and the current measurement resistor 26 is transferred via respectively separate systems constituted by the A/F ratio detection section 31 and the sensor element impedance detection section 32, appropriate (respectively separate) signal processing can be applied for deriving a signal indicative of the air/fuel ratio and a signal indicative of the sensor element impedance. Hence, appropriate processing can be applied, irrespective of the large difference in amplitude between these two signals, since the signals are amplified by separate systems.

In addition, it is unnecessary to apply two-stage amplification to the air/fuel ratio detection signal, and both air/fuel ratio detection and sensor element impedance detection can both be achieved to a high degree of accuracy.

Moreover, due to the fact that both air/fuel ratio detection and sensor element impedance detection are performed by measuring a voltage signal that appears at a common point (i.e., the junction between the sensor element 10 and the current measurement resistor 26) and varies with respect to the system ground potential, it becomes unnecessary to provide circuit elements for converting a differential voltage signal (e.g., appearing between the terminals of the resistance 63 in FIG. 10) to a signal that varies with respect to the system ground potential. Specifically, it is made unnecessary to use a circuit element such as the differential amplifier 65 in FIG. 10 to perform such conversion, as is required with prior art technology such as the circuit of FIG. 10, in which both an air/fuel ratio detection signal voltage and a sensor element impedance detection signal voltage are measured between the terminals of the resistor 63. Thus the present invention enables the overall circuit configuration to be simplified.

The above points will be described more specifically in the following. With the above embodiment, the output voltage from the operational amplifier 25 is an AC voltage whose average value (i.e., center value) is fixed at +2.2 V above ground potential. Hence, the air/fuel ratio can be detected by monitoring changes which occur in the average voltage appearing at the measurement point (i.e., junction between the sensor element 10 and the current measurement resistor 26), by extracting the DC component of the voltage variations at the measurement point. That is to say, a voltage signal is derived which varies with respect to the system ground potential.

On the other hand with the prior art technology of FIG. 10 for example, when the current flow through the current measurement resistor 63 varies as a result of the AC voltage superimposed by the oscillator 62 on the DC voltage from the reference voltage source 61 and as a result of the effects of changes in the air/fuel ratio on the sensor element 60, the voltage between the terminals of the current measurement resistor 63 will vary in accordance with these variations in current. Hence it is necessary to utilize the differential amplifier differential amplifier 65 to convert these changes in current flow to changes in voltage measured with respect to circuit ground potential.

Figure 1:
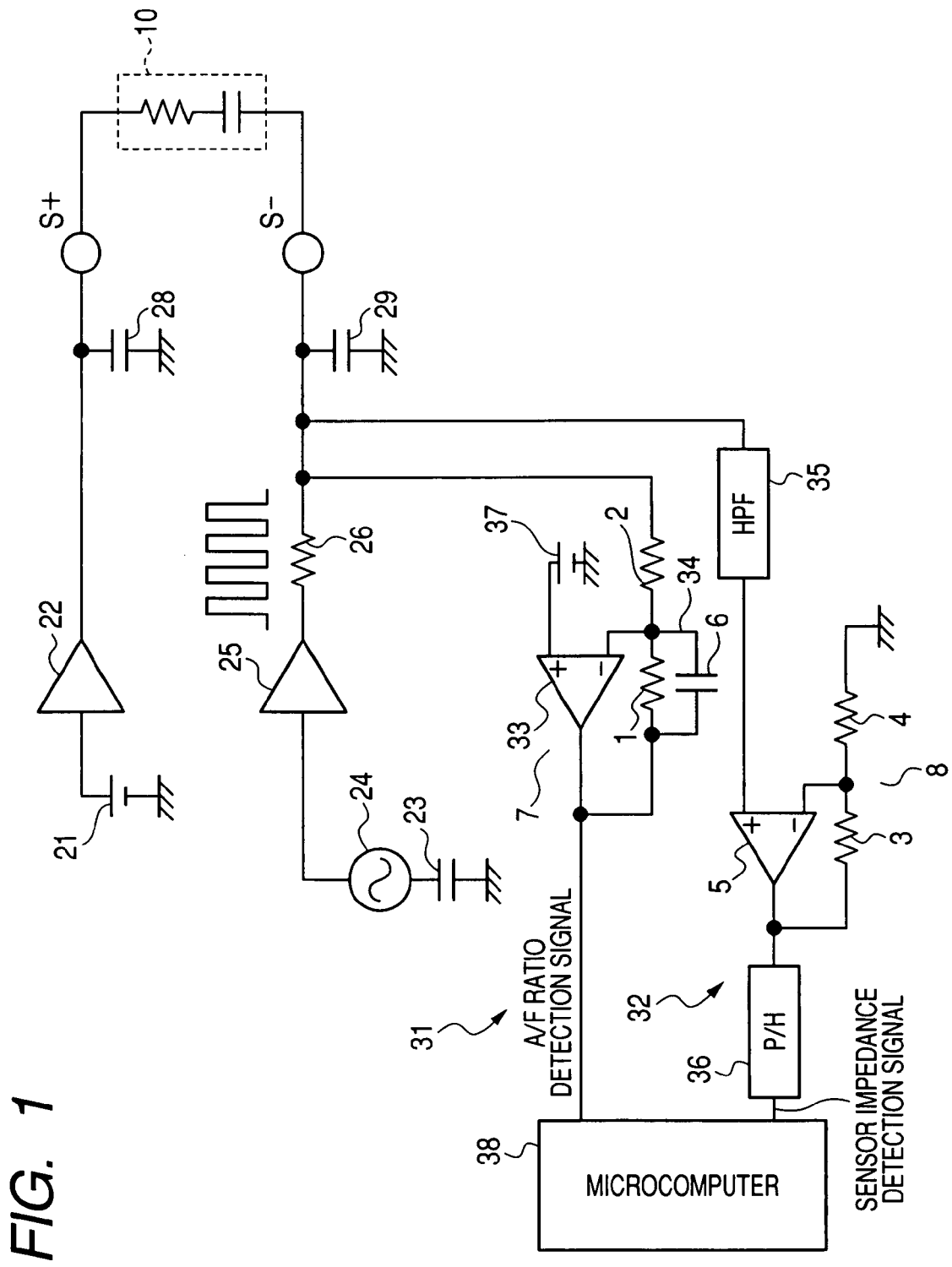
FIG. 1 is a circuit diagram showing the overall circuit configuration of a first embodiment of a gas concentration detection apparatus for application to engine exhaust gas.

With the circuit of the present invention shown in FIG. 1, however, with a signal indicative of the air/fuel ratio and a signal indicative of the elm impedance being extracted directly from a common point in the circuit, by respectively different systems, appropriate amplification can be applied to each of these signals to achieve accurate air/fuel ratio detection and sensor element impedance detection, without requiring the use of a differential amplifier. Appropriate signal processing can be applied for air/fuel ratio detection and sensor element impedance detection, in accordance with the processing range of the input circuits of a digital processor such as the microcomputer 38. Hence, the resolution of air/fuel ratio detection and sensor element impedance detection can be increased, by comparison with the prior art.

It should be noted that the invention is not limited to the above embodiment, and that for example the following alternative embodiments could be envisaged.

Figure 8A:
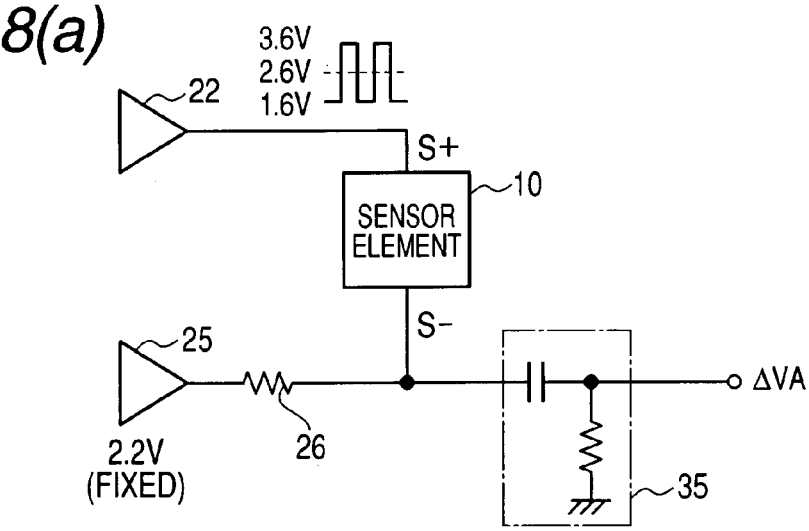
Figure 8A:
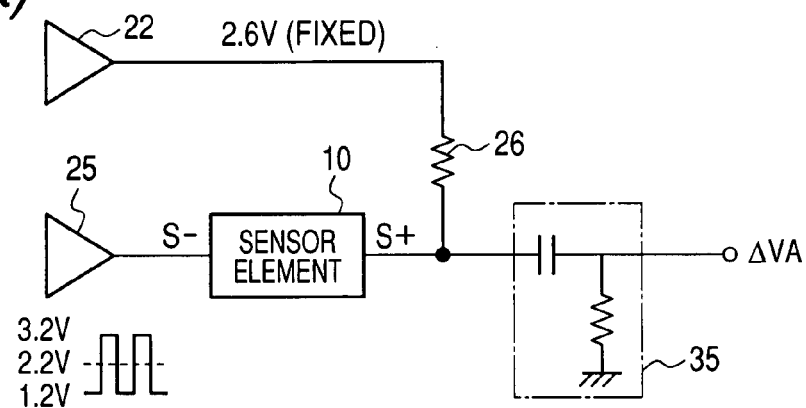
Figure 8C:
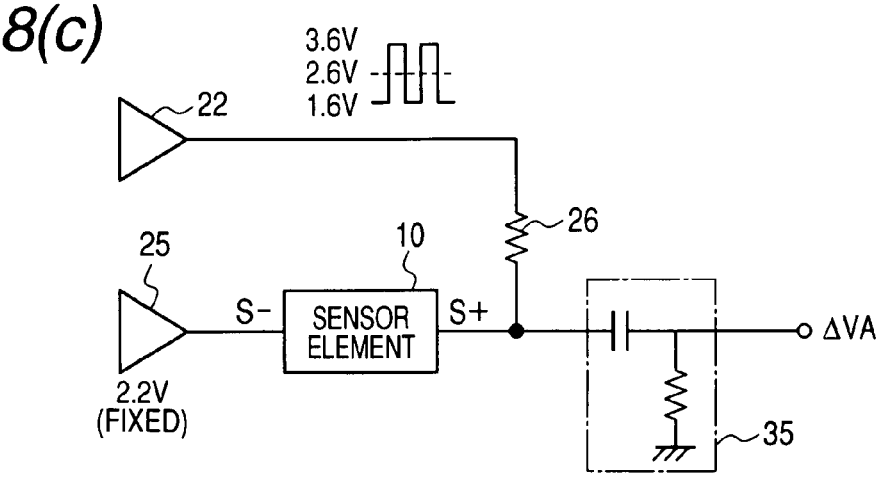

Firstly, with the above embodiment of FIG. 1, a fixed DC voltage (2.6 V) is applied to the S+ terminal of the sensor element 10, and an AC voltage with a DC bias (2.2 V±1 V) is applied to the S− terminal from the AC signal source (oscillator 24), with the current measurement resistor 26 being disposed between the AC signal source and the sensor element 10. However this could be changed to any of the alternative configurations for the first embodiment which are illustrated in FIGS. 8(a) to 8(c), described in the following. For brevity of description, simplified partial circuit diagrams of the form of FIG. 5 are utilized, with only the points of difference from the embodiment of FIG. 1 being described.

The configuration shown in FIG. 8(a) differs from that of FIG. 1 (FIG. 5) in that the AC voltage is applied to the S+ terminal of the sensor element 10 via the operational amplifier 22, with the 2.6 V fixed DC voltage of the reference voltage source 21 being set as the center (i.e., average) value of the AC voltage (which thus varies as 2.6 V±1 V), while the 2.2 V fixed DC voltage is applied to the S− terminal.

With the configuration of FIG. 8(b), the circuit locations of the current measurement resistor 26 and sensor element 10 are interchanged from those of the embodiment of FIG. 1, i.e., with the AC voltage (varying as 2.2 V±1 V) being applied to the S− terminal of the sensor element 10 and the 2.6 V fixed DC voltage being applied to the opposite terminal of the current measurement resistor 26 from the junction between the sensor element 10 and current measurement resistor 26.

With the configuration of FIG. 8(c), the circuit locations of the current measurement resistor 26 and sensor element 10 are interchanged from the configuration of FIG. 8(a), i.e., with the AC voltage (varying as 2.6 V±1 V) being applied to the opposite terminal of the current measurement resistor 26 from the junction between the sensor element 10 and current measurement resistor 26 and with the 2.2 V fixed DC voltage being applied to the S− terminal of the sensor element 10.

With each of the configurations of FIG. 8(a), FIG. 8(b) and FIG. 8(c), voltage signal components appearing at the junction between the sensor element 10 and the current measurement resistor 26 can be respectively extracted by the A/F ratio detection section 31 and the sensor element impedance detection section 32, as described for the first embodiment, to obtain the air/fuel ratio detection signal and the impedance detection signal from respective signal processing systems. Hence, the advantages described above for the first embodiment can also be obtained with each of the alternative configurations of FIGS. 8(a), 8(b) and 8(c).

Figure 9:
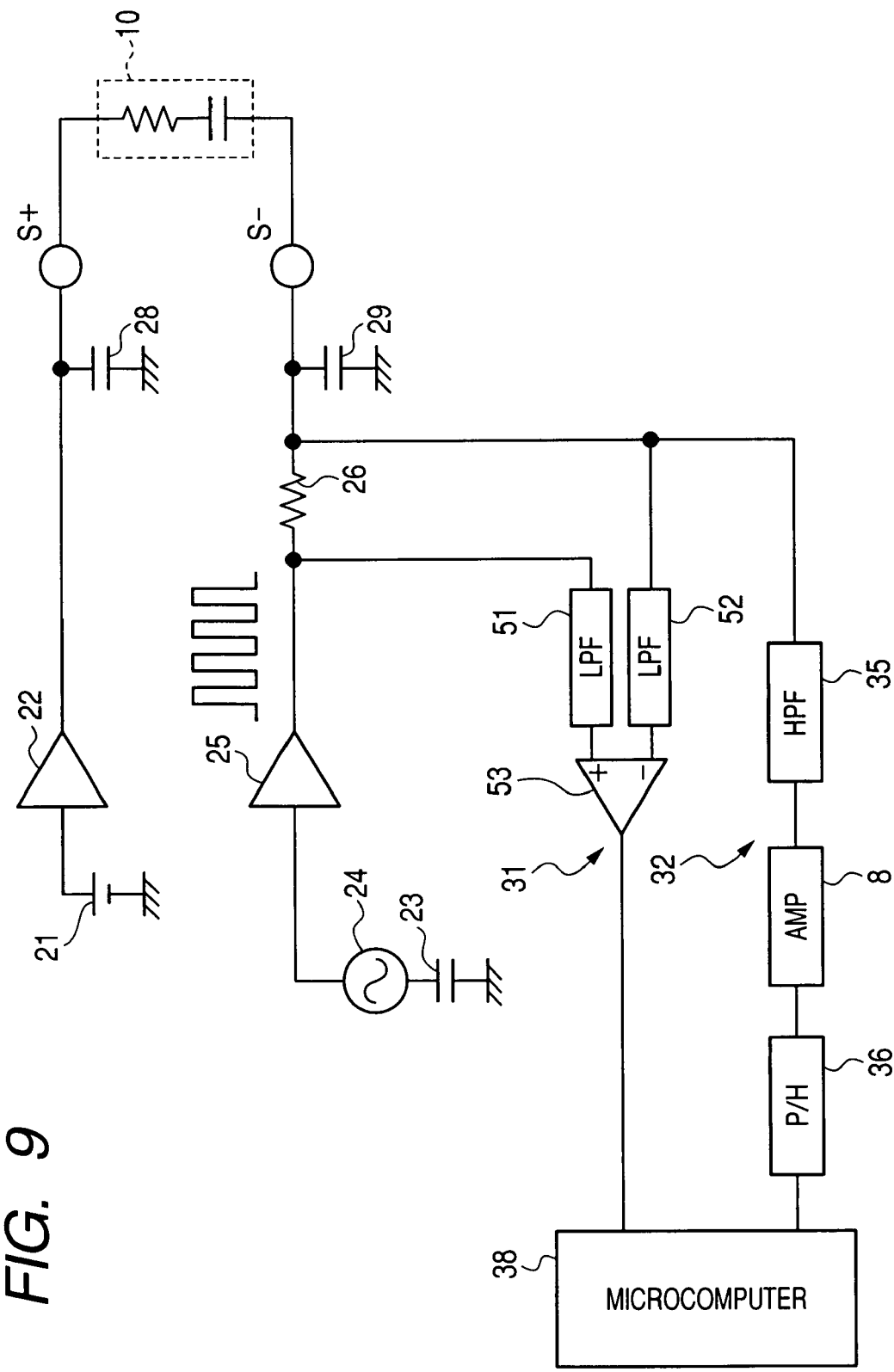
FIG. 9 is a circuit diagram of the overall circuit configuration of a second embodiment of a gas concentration detection apparatus for application to engine exhaust gas; and, FIG. 10 is a circuit diagram of a second example of a prior art type of gas concentration detection apparatus for application to engine exhaust gas.

The invention has been described above for the case in which the air/fuel ratio detection signal is extracted as a voltage signal component appearing at the junction between the sensor element 10 and the current measurement resistor 26, i.e., a voltage signal component which varies with respect to the circuit ground potential. However with a further alternative embodiment illustrated in FIG. 9, the air/fuel ratio detection signal can be extracted as a voltage signal component appearing between the terminals of the current measurement resistor 26. In FIG. 9, the input terminals of LPFs 51 and 52 are respectively connected to the opposing terminals of the current measurement resistor 26, with the output terminals of the LPFs 51 and 52 being connected to respective input terminals of a differential amplifier 53. The output signal thereby produced from the differential amplifier 53 is inputted to the microcomputer 38, as the air/fuel ratio detection signal.

As can be understood from the above description, the embodiment of FIG. 1, each of the alternative configurations of FIGS. 8(a), 8(b) and 8(c), and the embodiment of FIG. 9 each have the following basic features:

(a) An AC circuit path is formed (specifically, from the output terminal of the oscillator 24, through the current measurement resistor 26 and the sensor element 10, to the output terminal of the operational amplifier 22) to which an AC voltage is applied from the oscillator 24, causing an AC current component to flow in the AC circuit path.

(b) The sensor element impedance detection section 32 is connected to the junction between the current measurement resistor 26 and sensor element 10, to extract an AC voltage signal component corresponding to the AC current component. That is, the sensor element impedance detection section 32 is coupled to a point in the aforementioned AC circuit path, for extracting that AC voltage signal component.

(c) The A/F ratio detection section 31 is connected to at least one point in the AC circuit path (as a separate system from the sensor element impedance detection section 32), for extracting a DC voltage signal component corresponding to a DC current component which also flows in that circuit path, where the term "DC current component" has the significance defined hereinabove.

Alternatively viewed, the embodiment of FIG. 1, each of the alternative configurations of FIGS. 8(a), 8(b) and 8(c), and the embodiment of FIG. 9 all have the following basic features. The sensor element 10 and current measurement resistor 26 constitute a series-connected combination of circuit elements, with respective first terminals of the sensor element 10 and current measurement resistor 26 connected together at a connection point and with their respective second terminals constituting a pair of outer terminals of the series-connected combination. The reference voltage source 23 and oscillator 24 produce an AC voltage having an average value that differs from ground potential by a first amount, with the AC voltage being applied to a first one of the outer terminals. The reference voltage source 21 applies a fixed DC voltage which differs from ground potential by a second amount (different from the first amount) to a second one of the outer terminals. The A/F ratio detection section 31 is coupled to the aforementioned connection point, for extracting a DC component of the voltage appearing between the connection point and ground potential, to thereby derive the air/fuel ratio detection signal. Alternatively (FIG. 9) the A/F ratio detection section 31 is coupled to the opposing terminals of the current measurement resistor 26, for extracting the DC component. The sensor element impedance detection section 32 is coupled to the aforementioned connection point, for extracting an AC component of the voltage signal appearing at the connection point, to thereby derive the sensor impedance detection signal.

It should be noted that the present invention is not limited in scope to the detection of the air/fuel ratio of exhaust gas of an internal combustion engine, and is equally applicable to various other uses. For example, a compound type of gas concentration sensor has a plurality of cells, each formed of a solid electrolyte. A pump cell discharges oxygen contained in a gas that is being examined, and also detects the oxygen concentration. A second cell (sensor cell) detects the concentration of a specific constituent gas remaining after the oxygen has been discharged. Such a gas concentration sensor can be applied for example as a NOx sensor for detecting the concentration of nitrous oxide in the exhaust gas from a motor vehicle. The present invention would be applicable to increasing the accuracy of detecting concentrations of gases such as nitrous oxide and detecting sensor element impedance, with such types of gas concentration sensor.

Furthermore the invention would also be applicable to a type of gas concentration sensor which has, in addition to the above-described second cell (sensor cell), a third cell (referred to as a monitoring cell, or second pump cell). In that case, after the oxygen has been discharged, the third cell detects the concentration of residual oxygen.

The invention is moreover applicable to a type of gas concentration sensor that is capable of detecting concentrations of gaseous components such as hydrocarbons and carbon monoxide. With such a type of gas concentration sensor, a pump cell discharges excess oxygen contained in the gas that is under examination, and a sensor cell analyzes the gas remaining after removal of the excess oxygen, to detect the concentrations of hydrocarbons and carbon monoxide.

The invention is also applicable to types of gas concentration sensor other than those for use with a vehicle engine, and to types of gas concentration sensor for detection of gaseous components other than those contained in engine exhaust gas. When a gas concentration detection apparatus according to the present invention is applied to a gas other than the exhaust gas from a vehicle engine, it is preferable that the frequency of the AC voltage be set at a value within the range 1~20 kHz.

What is claimed is:

1. A gas concentration detection apparatus comprising
   a sensor element which incorporates a solid electrolyte layer and is responsive to an applied DC voltage for passing a concentration-indicative current varying in level in accordance with of a concentration of a specific constituent gas in a test-object gas,
   an AC voltage source and a DC voltage source for respectively applying an AC voltage and said DC voltage to said sensor element,
   a current measurement resistor connected in series with said sensor element in an AC current path through which an AC current component flows in response to said applied AC voltage, and
   a detection signal output circuit for deriving a gas concentration detection signal indicative of said concentration of the constituent gas based on said concentration-indicative current and deriving an impedance detection signal indicative of an impedance value of said sensor element based on said AC current component;
   wherein said detection signal output circuit comprises:
   a first detection signal output circuit for deriving said gas concentration detection signal, coupled to said current measurement resistor for extracting a first voltage signal, with said first voltage signal varying in level in accordance with said level of the concentration-indicative current, and
   a second detection signal output circuit for deriving said impedance detection signal, coupled to a connection point between said current measurement resistor and said sensor element for extracting a second voltage signal, which said second voltage signal being an AC signal which varies in amplitude with respect to a circuit ground potential in accordance with an amplitude of said AC current component.

2. A gas concentration detection apparatus according to claim 1, wherein said first detection signal output circuit and said second detection signal output circuit comprise respective amplifier circuits for amplifying said first voltage signal and second voltage signal, and wherein respective amplification factors of said amplifier circuits are predetermined separately from one another.

3. A gas concentration detection apparatus according to claim 1, wherein said first detection signal output circuit is coupled to a connection point between said current measurement resistor and said sensor element, for extracting said first voltage signal as a signal which varies with respect to a circuit ground potential.

4. A gas concentration detection apparatus according to claim 1, wherein said first detection signal output circuit is coupled to opposing terminals of said current measurement resistor, for extracting said first voltage signal as a differential voltage signal developed between said opposing terminals.

5. A gas concentration detection apparatus according to claim 1, comprising a calculation apparatus having an input circuit coupled to receive said gas concentration detection signal, wherein
   said first detection signal output circuit comprises a filter circuit for extracting said first voltage signal, and an amplifier circuit for amplifying an output signal from said filter circuit, to obtain said gas concentration detection signal, and
   said amplifier circuit is adapted to apply a fixed degree of amplification which is predetermined in accordance with an allowable range of input voltage signal values of said input circuit.

6. A gas concentration detection apparatus according to claim 1 comprising a calculation apparatus having an input circuit coupled to receive said gas concentration detection signal, wherein said second detection signal output circuit comprises
   a filter circuit for extracting said second voltage signal,
   an amplifier circuit for amplifying said second voltage signal, and
   a peak-hold circuit for detecting peak values of said second voltage signal component following said amplification,
   and wherein said amplifier circuit is adapted to apply a fixed degree of amplification which is predetermined based on an allowable range of input voltage signal values of said input circuit.

7. A gas concentration detection apparatus according to claim 1, wherein said AC voltage has a frequency that is fixed within a range from 1 kHz to 20 kHz.

8. A gas concentration detection apparatus comprising
   a gas concentration sensor element and a current measurement resistor coupled as a series-connected combination, said gas concentration sensor element being responsive to an applied DC voltage for passing a current at a level in accordance with a concentration of a gaseous constituent of a test-object gas, with respective first terminals of said sensor element and said current measurement resistor connected together at a connection point and with respective second terminals of said sensor element and said current measurement resistor constituting a pair of outer terminals of said series-connected combination;
   an AC voltage source producing an AC voltage having a fixed amplitude and fixed frequency and having an average value that differs from a ground potential of said apparatus by a first voltage amount, with said AC voltage being applied to a first one of said outer terminals,
   a reference voltage source producing a fixed DC voltage which differs from said ground potential by a second voltage amount, with said second voltage amount differing from said first voltage amount, said fixed DC voltage being applied to a second one of said outer terminals, a first detection signal output circuit coupled to said connection point, adapted to extract a first voltage signal component that varies with respect to said ground potential in accordance with a current resulting from said applied AC voltage, to amplify said first voltage signal component, and to detect peak values of said first voltage signal component following said amplification to thereby derive a detection signal indicative of an impedance of said sensor element, and a second detection signal output circuit coupled to said connection point, adapted to extract a second voltage signal component that varies with respect to said ground potential and varies within a frequency range that is substantially lower than a frequency of said AC voltage, and to amplify said second voltage signal component to thereby derive a detection signal indicative of said concentration of said constituent gas.

9. A gas concentration detection apparatus comprising a gas concentration sensor element and a current measurement resistor coupled as a series-connected combination, said gas concentration sensor element being responsive to an applied DC voltage for passing a current at a level in accordance with a concentration of a gaseous constituent of a test-object gas, with respective first terminals of said sensor element and said current measurement resistor connected together at a connection point and with respective second terminals of said sensor element and said current measurement resistor constituting a pair of outer terminals of said series-connected combination;

an AC voltage source producing an AC voltage having a fixed amplitude and fixed frequency and having an average value that differs from a ground potential of said apparatus by a first voltage amount, with said AC voltage being applied to a first one of said outer terminals, a reference voltage source producing a fixed DC voltage which differs from said ground potential by a second voltage amount, with said second voltage amount differing from said first voltage amount, said fixed DC voltage being applied to a second one of said outer terminals, a first detection signal output circuit coupled to said connection point, adapted to extract a first voltage signal that varies with respect to said ground potential in accordance with a current resulting from said applied AC voltage, to amplify said first voltage signal component, and to detect peak values of said first voltage signal component following said amplification to thereby derive a detection signal indicative of an impedance of said sensor element, and a second detection signal output circuit coupled to opposing terminals of said current measurement resistor, for extracting a second voltage signal as a differential voltage signal that is developed across said current measurement resistor and varies within a frequency range that is substantially lower than a frequency of said AC voltage, and to amplify said second voltage signal to thereby derive a detection signal indicative of said concentration of said constituent gas.

\* \* \* \* \*